United States Patent [19]

Smith

[11] 4,219,561

[45] Aug. 26, 1980

[54] ALKANOLAMINE DERIVATIVES

[75] Inventor: Leslie H. Smith, Macclesfield, England

[73] Assignee: Imperial Chemical Industries Limited, London, England

[21] Appl. No.: 942,815

[22] Filed: Sep. 15, 1978

[30] Foreign Application Priority Data

Sep. 22, 1977 [GB] United Kingdom ............... 39534/77

[51] Int. Cl.$^2$ ................... A61K 31/275; A61K 31/18; A61K 31/17; A61K 31/165
[52] U.S. Cl. .............................. 424/304; 260/553 A; 260/556 A; 260/559 T; 260/559 A; 424/250; 424/263; 424/270; 424/273 R; 424/274; 424/275; 424/285; 424/321; 424/322; 424/324
[58] Field of Search ............... 424/177, 304, 322, 324; 260/112.5 R, 465 D, 553 A, 553 E, 559 A, 559 T, 556 A

[56] References Cited

U.S. PATENT DOCUMENTS

| | | | |
|---|---|---|---|
| 3,928,412 | 12/1975 | Smith | 260/559 A |
| 3,930,016 | 12/1975 | Berntsson et al. | 260/553 A |
| 3,944,611 | 3/1976 | Smith | 260/559 A |
| 3,959,369 | 5/1976 | Smith | 260/553 R |
| 4,010,189 | 3/1977 | Smith | 260/465 D |
| 4,034,106 | 7/1977 | Smith | 424/304 |
| 4,035,420 | 7/1977 | Berntsson et al. | 260/553 A |
| 4,041,075 | 8/1977 | Smith | 260/553 A |
| 4,083,992 | 4/1978 | Smith | 424/303 |
| 4,115,409 | 9/1978 | Large et al. | 260/347.3 |

*Primary Examiner*—Frederick E. Waddell
*Attorney, Agent, or Firm*—Cushman, Darby & Cushman

[57] ABSTRACT

1-Aryloxy-3-(tri- or tetra-acylamido)-alkylamino-propan-2-ol derivatives, processes for their manufacture and pharmaceutical compositions containing them. The compounds possess β-adrenergic blocking activity and are useful in the treatment of heart diseases such as angina pectoris, cardiac arrhythmias and hypertension. Representative of the compounds disclosed is 1-(o-chlorophenoxy)-3-β-(phenylacetamido-γ-butyramido-γ-butyramido)-ethylamino-2-propanol.

10 Claims, No Drawings

ALKANOLAMINE DERIVATIVES

This invention relates to new alkanolamine derivatives which possess β-adrenergic blocking activity.

According to the invention there is provided a new alkanolamine derivative of the formula:

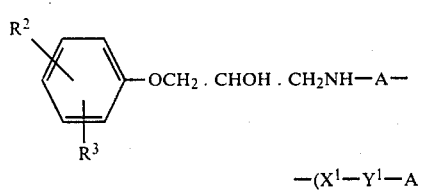

$$-(X^1-Y^1-A^1)_n-X^2-Y^2-R^1$$

wherein A stands for an alkylene radical of from 2 to 6 carbon atoms; wherein n stands for the integer 2 or 3, wherein $A^1$, the individual values of which may be the same or different, stands for an alkylene radical of up to 6 carbon atoms; wherein $R^1$ stands for the hydrogen atom or for an alkyl, halogenoalkyl, alkenyl or cycloalkyl radical each of up to 10 carbon atoms, or for an aryl radical of the formula:

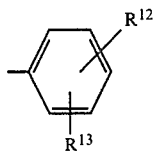

or for a heterocyclic radical; wherein $R^2$, $R^3$, $R^{12}$ and $R^{13}$, which may be the same or different, each stands for a hydrogen or halogen atom, a hydroxy, amino, nitro, carbamoyl or cyano radical, or an alkyl, alkenyl, alkoxy, alkylthio, alkenyloxy, alkanoyl or acylamino radical each of up to 6 carbon atoms, or wherein $R^2$ and $R^3$ together, and/or $R^{12}$ and $R^{13}$ together, form the trimethylene, tetramethylene or buta-1,3-dienylene radical such that together with the adjacent benzene ring they form respectively the indanyl, 5,6,7,8-tetrahydronaphthyl or naphthyl radical; wherein $X^1$ and $X^2$, the individual values of which may be the same or different, each stands for an amidic linkage of the formula —NHCO—, —NHSO$_2$— or —CONH—; wherein $Y^1$, the individual values of which may be the same or different, stands for a direct link or (except when $X^1$ is —CONH—) for the imino (—NH—) radical and wherein $Y^2$ stands for a direct link, or for an alkylene, oxyalkylene or alkyleneoxy radical each of up to 6 carbon atoms, or (except when $X^2$ is —CONH—) for the imino (—NH—) radical or for an alkylimino or iminoalkylene radical each of up to 6 carbon atoms, or (except when $R^1$ stands for the hydrogen atom) for the oxygen atom; or an acid-addition salt thereof.

It will be observed that the alkanolamine derivative of the invention possesses an asymmetric carbon atoms, namely the carbon atom of the —CHOH— group in the alkanolamine side-chain, and it can therefore exist in racemic and opticaly-active forms. It is to be understood that this invention encompasses the racemic form of the alkanolamine derivative and any optically-active form which possesses β-adrenergic blocking activity, it being a matter of common general knowledge how a racemic compound may be resolved into optically-active forms, and how the β-adrenergic blocking activity of these forms may be determined. It is further to be understood that β-adrenergic blocking activity usually predominates in that optically-active form which has the "S" absolute configuration of the said —CHOH— group.

A suitable value for the alkylene radical A is, for example, the ethylene, trimethylene, tetramethylene, hexamethylene, 1-methylethylene, 2-methylethylene or 1,1-dimethylethylene radical. A is preferably the ethylene, 1-methylethylene or 1,1-dimethylethylene radical, especially the ethylene radical.

A suitable value for the alkylene radical $A^1$ is, for example, the methylene or ethylidene radical or one of the values set out above for the alkylene radical A. $A^1$ is preferably the methylene, ethylene or trimethylene radical.

A suitable value for $R^1$ when it stands for an alkyl, halogenalkyl, alkenyl or cycloalkyl radical is, for example, the methyl, ethyl, n-propyl, isopropyl, n-butyl, isobutyl, t-butyl, n-pentyl, n-octyl, trifluoromethyl, allyl, cyclopropyl, cyclopentyl or cyclohexyl radical. A preferred value for $R^1$ from this group of values is the methyl, isopropyl or t-butyl radical.

A suitable value for $R^1$ when it stands for a heterocyclic radical is, for example, a 5 or 6-membered saturated or unsaturated monocyclic heterocyclic radical containing one or two heteroatoms selected from nitrogen, oxygen or sulphur atoms, which heterocyclic radical may optionally contain one or two substituents selected from alkyl and alkoxy radicals each of up to 6 carbon atoms, for example methyl, ethyl, methoxy and ethoxy radicals and, where the heterocyclic radical bears an appropriate degree of saturation, one or two oxo substituents.

A particular heterocyclic radical is, for example, a pyrrolyl, furyl, thienyl, imidazolyl, thiazolyl, pyridyl, pyrazinyl or pyridazinyl radical, for example the 2-pyrrolyl, 2-furyl, 2-thienyl, 3-thienyl, 2-imidazolyl, 2-thiazolyl, 4-pyridyl, 3-methyl-2-pyrazinyl or 2-pyridazinyl radical. A preferred heterocyclic radical $R^1$ is the 2-thienyl or 2-furyl radical.

A suitable value for $R^2$, $R^3$, $R^{12}$ or $R^{13}$ when it stands for a halogen atom is for example, the fluorine, chlorine, bromine or iodine atom.

A suitable value for $R^2$, $R^3$, $R^{12}$ or $R^{13}$ when it stands for an alkyl, alkenyl, alkoxy, alkylthio, alkenyloxy, alkanoyl or acylamino radical is, for example, the methyl, ethyl, n-propyl, allyl, methoxy, isopropoxy, methylthio, allyloxy, formyl, acetyl or acetamido radical.

An especially preferred value for $R^1$ is the unsubstituted phenyl radical, that is, $R^{12}$ and $R^{13}$ are both hydrogen atoms.

$R^2$ is preferably the chlorine atom or the cyano, methyl or methoxy radical, this substituent preferably being in the 2-position of the phenyl nucleus, and $R^3$ is preferably the hydrogen atom.

$X^1$ and $X^2$ are preferably both the —NHCO— radical.

A suitable value for $Y^2$ when it stands for an alkylene, oxyalkylene or alkyleneoxy radical is, for example, the methylene, ethylene, oxymethylene, methyleneoxy, ethyleneoxy, trimethyleneoxy, 1-methylethylideneoxy or 1-methylpropylideneoxy radical.

A suitable value for $Y^2$ when it stands for an alkylimino or iminoalkylene radical is, for example, the methylimino or iminomethylene radical.

$Y^1$ is preferably a direct link and $Y^2$ is preferably a direct link or the methylene, oxymethylene, methyleneoxy or imino radical, especially the methylene or oxymethylene radical.

A suitable acid-addition salt of an alkanolamine derivative of the invention is, for example, a salt derived from an inorganic acid, for example a hydrochloride, hydrobromide, phosphate or sulphate, or a salt derived from an organic acid, for example an oxalate, lactate, tartrate, acetate, salicylate, citrate, benzoate, β-naphthoate, adipate or 1,1-methylene-bis-(2-hydroxy-3-naphthoate), or a salt derived from an acidic synthetic resin, for example a sulphonated polystyrene resin A preferred alkanolamine derivative of the invention is a compound of the formula given above wherein A stands for the ethylene radical, n stands for the integer 2, $A^1$ stands for the methylene, ethylene or trimethylene radical, $R^1$ stands for the unsubstituted phenyl radical (that is, $R^{12}$ and $R^{13}$ both stand for hydrogen), $R^2$ stands for hydrogen, or for the chloro or cyano radical or for an alkyl or alkoxy radical each of up to 3 carbon atoms in the 2-position of the phenyl nucleus, $R^3$ stands for hydrogen, $X^1$ stands for the —NHCO— radical, $X^2$ stands for the —NHCO— radical, $Y^1$ stands for a direct link and $Y^2$ stands for the methylene or oxymethylene radical, or is an acid-addition salt thereof.

Specific alkanolamine derivatives of the invention are those hereinafter described in the Examples. Of these preferred compounds by virtue of their high cardioselective β-adrenergic blocking activity (as hereinafter defined) are 1-(o-methoxyphenoxy)-3-β-(phenylacetamidoacetamidoacetamido)-ethylamino-2-propanol and 1-(o-chlorophenoxy)-3-β-(phenylacetamido-γ-butyramido-γ-butyramido)-ethylamino-2-propanol and the acid-addition salts thereof.

The alkanolamine derivatives of the invention may be manufactured by any chemical process known to be useful for the manufacture of chemically-analogous compounds.

A preferred process for the manufacture of an alkanolamine derivative of the invention wherein the radical $X^1$ nearest to the radical A stands for the radical —NH—CO— comprises the reaction of a compound of the formula:

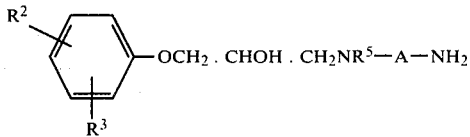

wherein A, $R^2$ and $R^3$ have the meanings stated above and wherein $R^5$ stands for hydrogen or for the benzyl radical, either with a compound of the formula:

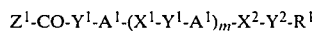

wherein $A^1$, $R^1$, $X^2$, $Y^1$ and $Y^2$ have the meanings stated above, wherein m stands for the integer 1 or 2 and wherein $Z^1$ stands for a displaceable radical;

or, when the radical $Y^1$ nearest to the radical A is the imino radical, with an isocyanate of the formula:

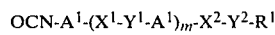

wherein $A^1$, $R^1$, $X^1$, $X^2$, $Y^1$, $Y^2$ and m have the meanings stated above, whereafter if $R^5$ stands for the benzyl radical this radical is removed by hydrogenolysis.

The displaceable radical $Z^1$ may be, for example, a halogen atom, for example the chlorine or bromine atom, or a sulphonyloxy radical, for example an alkanesulphonyloxy radical of up to 6 carbon atoms or an arenesulphonyloxy radical of up to 10 carbon atoms, for example the methanesulphonyloxy, benzenesulphonyloxy or toluene-p-sulphonyloxy radical, or an alkoxy, alkoxycarbonyl or aryloxy radical of up to 10 carbon atoms, for example the methoxy, ethoxy, ethoxycarbonyl, phenoxy or 2,4,5-trichlorophenoxy radical. Alternatively, $Z^1$ may be the hydroxy radical, in which case the reaction is carried out in the presence of a condensing agent, for example a carbodi-imide.

A compound wherein one or more of $R^2$, $R^3$, $R^{12}$ and $R^{13}$ stands for the hydroxy radical may be obtained by the hydrogenolysis of the corresponding compound wherein one or more of $R^2$, $R^3$, $R^{12}$ and $R^{13}$ stands for the benzyloxy radical.

Optically-active enantiomorphs of the alkanolamine derivative of the invention may be obtained by the resolution by conventional means of the corresponding racemic alkanolamine derivative of the invention.

The said resolution may be carried out by reacting the racemic alkanolamine derivative with an optically-active acid, followed by fractional crystallisation of the diastereoisomeric mixture of salts thus obtained from a diluent or solvent, for example ethanol, whereafter the optically-active alkanolamine derivative is liberated from the salt by treatment with a base. A suitable optically-active acid is, for example (+)- or (−)-O,O-di-p-toluoyltartaric acid or (−)-2,3:4,5-di-O-isopropylidene-2-keto-L-gulonic acid.

The resolution process may be facilitated by treating the partially resolved alkanolamine derivative in free base form obtained after a single fractional crystallisation of the diastereoisomeric mixture of salts with a solubilising agent, for example a primary amine, for example allylamine, in a relatively non-polar diluent or solvent, for example petroleum ether.

The alkanolamine derivative of the invention in free base form may be converted into an acid-addition salt thereof by reaction with an acid by conventional means.

As stated above, the alkanolamine derivative of the invention or an acid-addition salt thereof possesses β-adrenergic blocking activity, and furthermore this activity is cardioselective. This activity may be determined by the reversal of isoprenaline-induced tachycardia in rats or cats, a standard test for the determination of β-adrenergic blocking activity, and by relative freedom from antagonism of isoprenaline-induced vasodilation in cats or of the relief produced by isoprenaline of histamine-induced bronchospasm in guinea-pigs. Compounds exhibiting this cardioselective action show a greater degree of specificity in blocking the cardiac β-receptors than the β-receptors in peripheral blood vessels and bronchial muscle. Thus, a dose may be selected for such a compound at which the compound blocks the cardiac inotropic and chronotropic actions of a catecholamine such as isoprenaline but does not block the relaxation of tracheal smooth muscle produced by isoprenaline or the peripheral vasodilator action of isoprenaline. Because of this selective action, one of these compounds may advantageously be used together with a sympathomimetic bronchodilator, for example isoprenaline, orciprenaline, adrenaline or ephedrine, in the treatment of asthma and other obstructive airways diseases, inasmuch as the cardioselective compound will substantially inhibit the unwanted stimulatory effects of the bronchodilator on the heart but will not hinder the desirable therapeutic effect of the bronchodilator. A preferred alkanolamine derivative of the invention is up to ten times more active as a cardioselective $\beta$-adrenergic blocking agent than practolol. At doses of an alkanolamine derivative of the invention which produce effective $\beta$-adrenergic blockade in rats or cats, no symptoms of toxicity are apparent.

The alkanolamine derivative of the ivention may be administered to warm-blooded animals including man, in the form of a pharmaceutical composition comprising as active ingredient at least one alkanolamine derivative of the invention, or an acid-addition salt thereof, in association with a pharmaceutically-acceptable diluent or carrier therefor.

A suitable composition is, for example, a tablet, capsule, aqueous or oily solution or suspension, emulsion, injectable aqueous or oily solution or suspension, dispersible powder, spray or aerosol formulation.

The pharmaceutical composition may contain, in addition to the alkanolamine derivative of the invention, one or more drugs selected from sedatives, for example phenobarbitone, meprobamate, chlorpromazine and the benzodiazepine sedative drugs, for example chlordiazepoxide and diazepam; vasodilators, for example glyceryl trinitrate, pentaerythritol tetranitrate and isosorbide dinitrates; diuretics, for example chlorothiazides; hypotensive agents, for example reserpine, bethanidine and guanethidine; cardiac membrane stabilising agents, for example quinidine; agents used in the treatment of Parkinson's disease and other tremors, for example benzhexol; cardiotonic agents, for example digitalis preparations; $\alpha$-adrenergic blocking agents, for example phentolamine and sympathomimetic bronchodilators, for example isoprenaline, orciprenaline, adrenaline and ephedrine.

When used for the treatment of heart diseases, for example angina pectoris and cardiac arrhythmias, or for the treatment of hypertension or anxiety states in man, it is expected that the alkanolamine derivative would be given to man at a total oral dose of between 20 mg. and 600 mg. daily, at doses spaced at 6–8 hourly intervals, or at an intravenous dose of between 1 mg. and 20 mg.

Preferred oral dosage forms are tablets or capsules containing between 10 and 100 mg., and preferably 10 mg. or 50 mg. of active ingredient. Preferred intravenous dosage forms are sterile aqueous solutions of the alkanolamine derivative or of a non-toxic acid-addition salt thereof, containing between 0.05% and 1% w/v of active ingredient, and more particularly containing 0.1% w/v of active ingredient.

The invention is illustrated but not limited by the following Examples:

Example 1

A mixture of 1-(o-tolyloxy)-3-($\beta$-aminoethyl)amino-2-propanol (2.5 g.) and N-phenylacetylglycylglycine methyl ester (2.6 g.) is heated at 90° C. for 2.5 hours and then cooled. The residue is crystallised from acetonitrile and there is thus obtained 1-(o-tolyloxy)-3-$\beta$-(phenylacetamido-acetamidoacetamido)ethylamino-2-propanol, m.p. 123°–125° C.

The process described above is repeated except that the appropriate N-acylglycylglycine methyl ester and the appropriate 1-phenoxy-3-($\beta$-aminoethyl)amino-2-propanol are used as starting materials. There are thus obtained the compounds shown in the following table:

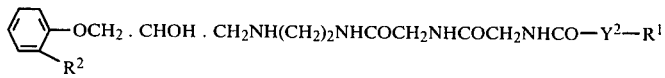
$$\text{C}_6\text{H}_4(\text{R}^2)\text{—OCH}_2\cdot\text{CHOH}\cdot\text{CH}_2\text{NH}(\text{CH}_2)_2\text{NHCOCH}_2\text{NHCOCH}_2\text{NHCO—Y}^2\text{—R}^1$$

| $R^2$ | $-Y^2R^1$ | m.p. °C. | Crystallisation solvent |
| --- | --- | --- | --- |
| cyano | $-CH_2C_6H_5$ | oxalate 199–200 | ethanol |
| methoxy | $-CH_2C_6H_5$ | 124–126 | acetonitrile |
| methyl | $-OCH_2C_6H_5$ | hydrochloride 143–144 | ethanol |
| methoxy | $-OCH_2C_6H_5$ | hydrochloride 108–111 | ethanol |
| carbamoyl | $-OCH_2C_6H_5$ | hydrochloride 150–152 | ethanol/ether |

The N-phenylacetylglycylglycine methyl ester used as starting material may be obtained as follows:

A solution of glycine methyl ester (56.5 g.) and triethylamine (62.3 ml.) in chloroform (250 ml.) is added dropwise to a stirred solution of N-phenylacetamidoglycine (89.3 g.), morpholine (58.8 ml.) and ethyl chloroformate (43.2 ml.) in chloroform (1 liter) which is maintained at −10° C. to −5° C. The solution is stirred for 30 minutes, the temperature is then allowed to rise to laboratory temperature and the mixture is stirred for 18 hours. The solution is then washed successively with aqueous N-hydro chloric acid (1 liter), water (1 liter), aqueous 1 N-sodium bicarbonate solution (1 liter) and water (1 liter). The chloroform solution is then dried over anhydrous magnesium sulphate and evaporated to dryness under reduced pressure. The residue is crystallised from isopropanol and there is thus obtained N-phenylacetylglycylglycine methyl ester, m.p. 132°–134° C.

EXAMPLE 2

A mixture of 1-(o-chlorophenoxy)-3-($\beta$-aminoethyl)-amino-2-propanol (2.7 g.) and N-phenylacetyl-$\beta$-alanyl-$\beta$-alanine methyl ester (2.9 g.) is heated at 140° C. for 3.5 hours and then cooled. The residue is crystallised from ethanol and there is thus obtained 1-(o-chlorophenoxy)-3-$\beta$-(phenylacetamido-$\beta$-propionamido-$\beta$-propionamido)-ethylamino-2-propanol, m.p. 140°–142° C.

The process described above is repeated except that 1-(o-tolyloxy)- or 1-(o-cyanophenoxy)-3-($\beta$-aminoethyl)amino-2-propanol derivative is used as starting material. There are thus obtained 1-(o-tolyloxy)-3-$\beta$-

(phenylacetamido-β-propionamido-β-propionamido)ethylamino-2-propanol, m.p. 136°-138° C. and 1-(o-cyanophenoxy)-3-β-(phenylacetamido-β-propionamido-β-propionamido)-ethylamino-2-propanol, m.p. 145°-148° C.

The N-phenylacetyl-β-alanyl-β-alanine methyl ester (m.p. 143°-145° C.) using as starting material may be obtained by a similar method to that described in the last part of Example 1, using β-anlanine methyl ester and N-phenylacetamido-β-alanine as intermediates.

EXAMPLE 3

A mixture of 1-(o-tolyloxy)-3-(β-amino ethyl)amino-2-propanol (0.48 g.) and N-phenylacetyl-β-alanylglycine methyl ester (0.6 g.) is heated at 90° C. for 2.5 hours and then cooled. The residue is crystallised from ethanol and there is thus obtained 1-(o-tolyloxy)-3-β-(phenylacetamido-β-propionamidoacetamido)ethylamino-2-propanol, m.p. 129°-131° C.

The process described above is repeated except that N-phenylacetylglycyl-β-alanine methyl ester is used as starting material. There is thus obtained 1-(o-tolyloxy)-3-β-phenylacetamidoacetamido-β-propionamidoethylamino-2-propanol, m.p. 120°—122° C.

The N-phenylacetyl-β-alanylglycine methyl ester used as starting material may be obtained as follows:

To a stirred solution of glycine methyl ester hydrochloride (1.3 g.) in tetrahydrofuran (100 ml.) at laboratory temperatures there are added, consecutively, triethylamine (1.0 g.), N-phenylacetyl-β-alanine (2.1 g.) and N-ethoxycarbonyl-2-ethoxy-1,2-dihydroquinoline (2.6 g.) and the mixture is stirred at laboratory temperature for 18 hours. The mixture is filtered and the filtrate is evaporated to dryness under reduced pressure. The residue is triturated with ether (50 ml.) and the mixture is filtered. The solid residue is stirred wtih a mixture of ethyl acetate (25 ml.) and petroleum ether (b.p. 60°-80° C., 25 ml.) and the mixture is filtered. The solid residue consists of N-phenylacetyl-β-alanylglycine methyl ester, m.p. 110°-112° C.

The N-phenylacetyl-glycyl-β-alanine methyl ester, m.p. 134°-136° C., may be prepared in a similar manner.

EXAMPLE 4

A solution of 1-(o-tolyloxy)-3-(β-aminoethyl)amino-2-propanol (3.0 g.) and N-phenylacetyl-γ-butyramido-β-alanine methyl ester (4.0 g.) in methanol (15 ml.) is evaporated to dryness and the residue is heated at 90° C. under vacuum for 48 hours. The residue is crystallised from acetonitrile and there is thus obtained 1-(o-tolyloxy)-3-β-(phenylacetamido-γ-butyramido-β-propionamido)ethylamino-2-propanol, m.p. 119°-121° C.

The process described above is repeated except that 1-(o-chlorophenoxy)-3-(β-aminoethyl)amino-2-propanol (0.9 g.) and N-phenylacetyl-γ-butyramido-γ-butyric acid methyl ester (1.2 g.) are used as starting materials. There is thus obtained 1-(o-chlorophenoxy)-3-β-(phenylacetamido-γ-butyramido-γ-butyramido)ethylamino-2-propanol, m.p. 114°-116° C.

The N-phenylacetyl-γ-butyramido-β-alanine methyl ester (m.p. 131°-134° C.) and the N-phenylacetyl-γ-butyramido-γ-butyric acid methyl ester (m.p. 111°-113° C.) used as starting materials may be obtained by a similar process to that described in the last part of Example 3.

What we claim is:

1. An alkanolamine derivative of the formula:

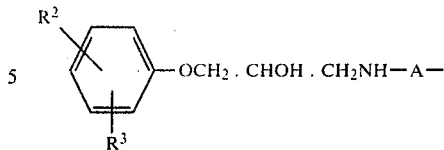

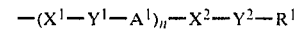

wherein A stands for an alkylene radical of from 2 to 6 carbon atoms; wherein n stands for the integer 2 or 3, wherein $A^1$, the individual values of which may be the same or different, stands for an alkylene radical of up to 6 carbon atoms; wherein $R^1$ stands for the hydrogen atom or for an alkyl, haloenoalkyl, alkenyl or cycloalkyl radical each of up to 10 carbon atoms, or for an aryl radical of the formula:

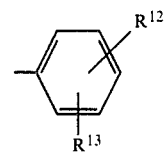

wherein $R^2$, $R^3$, $R^{12}$ and $R^{13}$, which may be the same or different, each stands for a hydrogen or halogen atom, a hydroxy, amino, nitro, carbamoyl or cyano radical, or an alkyl, alkenyl, alkoxy, alkylthio, alkenyloxy, alkanoyl or acylamino radical each of up to 6 carbon atom, or wherein $R^2$ and $R^3$ together, and/or $R^{12}$ and $R^{13}$ together, form the trimethylene, tetramethylene or buta-1,3-dienylene radical such that together with the adjacent benzene ring they form respectively the indanyl, 5,6,7,8-tetrahydronaphthyl or naphthyl radical; wherein $X^1$ and $X^2$, the individual values of which may be the same or different, each stands for an amidic linkage of the formula —NHCO— or —CONH—; wherein $Y^1$, the individual values of which may be the same or different, stands for a direct link or (except when $X^1$ is —CONH—) for the imino (—NH—) radical and wherein $Y^2$ stands for a direct link, or for an alkylene, oxyalkylene or alkyleneoxy radical each of up to 6 carbon atoms, or (except when $X^2$ is —CONH—) for the imino (—NH—) radical or for an alkylimino or iminoalkylene radical each of up to 6 carbon atoms, or (except when $R^1$ stands for the hydrogen atom) for the oxygen atom; or an acid-addition salt thereof.

2. An alkanolamine derivative as claimed in claim 1 wherein A stands for the ethylene, trimethylene, tetramethylene, hexamethylene, 1-methylethylene, 2-methylethylene or 1,1-dimethylethylene radical, wherein $A^1$ stands for the methylene or ethylidene radical or one of the values set out above for the alkylene radical A, wherein n stands for the integer 2 or 3, wherein $R^1$ stands for the hydrogen atom or for the methyl, ethyl, n-propyl, isopropyl, n-butyl, isobutyl, t-butyl, n-pentyl, n-octyl, trifluoromethyl, allyl, cyclopropyl, cyclopentyl or cyclohexyl radical, or for anaryl radical of the formula:

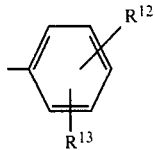

wherein R², R³, R¹² and R¹³, which may be the same or different, each stands for a hydrogen, fluorine, chlorine, bromine or iodine atom or for the hydroxy, amino, nitro, carbamoyl, cyano, methyl, ethyl, n-propyl, allyl, methoxy, isopropoxy, methylthio, allyloxy, formyl, acetyl or acetamido radical, or wherein R² and R³, and/or R¹² and R¹³, together with the adjacent benzene ring form the indanyl, 5,6,7,8-tetrahydronaphtyl or naphthyl radical, wherein X¹ and X² are both the —NHCO— radical, wherein Y¹ is a direct link or the imino radical and wherein Y² is a direct link or the methylene, ethylene, oxymethylene, methyleneoxy, ethyleneoxy, trimethyleneoxy, 1-methylethylideneoxy, 1-methylpropylideneoxy, imino, methylamino or iminomethylene radical, or an acid-addition salt thereof.

3. An alkanolamine derivative as claimed in claim 2 wherein A stands for the ethylene, 1-methylethylene or 1,1-dimethylethylene radical, wherein A¹ stands for the methylene, ethylene or trimethylene radical, wherein n stands for the integer 2 or 3, wherein R¹ stands for the methyl, isopropyl, t-butyl or phenyl, radical, wherein R² stands for the hydrogen atom or the chlorine atom or the cyano, methyl or methoxy radical in the 2-position of the phenyl nucleus, and R³ stands for the hydrogen atom, wherein X¹ and X² are both the —NHCO— radical, Y¹ is a direct link and Y² is a direct link or the methylene, oxymethylene, methyleneoxy or imino radical, or an acid-addition salt thereof.

4. An alkanolamine derivative as claimed in claim 1 wherein A stands for the ethylene radical, n stands for the integer 2, A¹ stands for the methylene, ethylene or trimethylene radical, R¹ stands for the unsubstituted phenyl radical, R² stands for hydrogen or for the chloro or cyano radical or for an alkyl or alkoxy radical each of up to 3 carbon atoms in the 2-position of the phenyl nucleus, R³ stands for the hydrogen atom, X¹ stands for the —NHCO— radical, X² stands for the —NHCO— radical, Y¹ stands for a direct link and Y² stands for the methylene or oxymethylene radical, or an acid-addition salt thereof.

5. The compound 1-(o-methoxyphenoxy)-3-β-(phenylacetamidoacetamidoacetamido)-ethylamino-2-propanol or an acid-addition salt thereof.

6. The compound 1-(o-chlorophenoxy)-3-β-(phenylacetamido- -butyramido- butyramido)ethylamino-2-propanol or an acid-addition salt thereof.

7. An acid-addition salt is claimed in claim 1 which is a hydrochloride, hydrobromide, phosphate, sulphate, oxalate, lactate, tartrate, acetate, salicylate, citrate, benzoate, β-naphthoate, adipate or 1,1-methylene-bis-(2-hydroxy-3-naphthoate), or a salt derived from a sulphonated polystyrene resin.

8. A pharmaceutical composition for the treatment or prophylaxis of heart diseases or hypertension comprising as active ingredient an effective amount of at least one alkanolamine derivative or an acid-addition salt thereof, claimed in claim 1, in association with a pharmaceutically-acceptable diluent or carrier therefor.

9. A method for the treatment or prophylaxis of heart diseases and hypertension in a warm-blooded animal which comprises administering to said animal an effective amount of at least one compound claimed in claim 1.

10. A method for producing coronary β-adrenergic blockade in a warm-blooded animal in need of such blockade which comprises administering to said animal an effective amount of at least one compound claimed in claim 1.

* * * * *